(12) United States Patent
Chen

(10) Patent No.: US 9,364,535 B2
(45) Date of Patent: Jun. 14, 2016

(54) METHODS AND COMPOSITIONS FOR MODULATING LYMPHANGIOGENESIS, E.G., TO TREAT TRANSPLANT REJECTION, IN A SUBJECT

(71) Applicant: The Regents of the University of California, Oakland, CA (US)

(72) Inventor: Lu Chen, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 177 days.

(21) Appl. No.: 13/966,760

(22) Filed: Aug. 14, 2013

(65) Prior Publication Data
US 2014/0050742 A1    Feb. 20, 2014

Related U.S. Application Data

(60) Provisional application No. 61/683,635, filed on Aug. 15, 2012.

(51) Int. Cl.
*C07K 16/28* (2006.01)
*A61K 39/395* (2006.01)
*A61K 39/00* (2006.01)

(52) U.S. Cl.
CPC .......... *A61K 39/3955* (2013.01); *C07K 16/2842* (2013.01); *C07K 16/2863* (2013.01); *A61K 2039/507* (2013.01); *C07K 2317/76* (2013.01)

(58) Field of Classification Search
CPC .................... A61K 39/3955; A61K 2039/507; C07K 16/2842; C07K 16/2863; C07K 2317/76
See application file for complete search history.

(56) References Cited

U.S. PATENT DOCUMENTS

2003/0180294 A1* 9/2003 DeVries .................... 424/143.1

FOREIGN PATENT DOCUMENTS

WO    WO 2005/016883 A2    2/2005
WO    WO 2005/019177 A1    3/2005

OTHER PUBLICATIONS

Chen et al., Arch Ophthalmol 125(6): 783-788, Jun. 2007.*
Zhang et al., Investigative Ophthalmology & Visual Science 52(9): 6529-6535, Aug. 17, 2011.*
Chen et al., Nature Medicine 10(8): 813-815, Aug. 2004.*
Golay et al., Archives of Biochemistry and Biophysics 526: 146-153, 2012.*
Cochran et al., J. Immunol. Meth. 287: 147-158, 2004.*
Yu et al., Investigative Ophthalmology & Visual Science 49(2): 522-527, Feb. 2008.*
Witte et al., Cancer and Metastasis Reviews 17: 155-161, 1998.*
Colman et al., in Research in Immunology (145(1):33-35, 1994.*
Nykanen et al., Circulation 121: 1413-1422, 2010.*
Chen et al., "Vascular endothelial growth factor receptor-3 mediates induction of corneal alloimmunity", Nature Medicine, vol. 10, No. 8, pp. 813-815 (2004).
Chen et al., "Very Late Antigen 1 Blockade Markedly Promotes Survival of Corneal Allografts", Arch Ophthalmol., vol. 125, pp. 783-788 (2007).
Ecoiffier et al., "Differential Distribution of Blood and Lymphatic Vessels in the Murine Cornea", Investigative Ophthalmology & Visual Science, vol. 51, No. 5, pp. 2436-2440 (2010).
Gerwins et al., "Function of fibroblast growth factors and vascular endothelial growth factors and their receptors in angiogenesis", Critical Reviews in Oncology/Hematology, vol. 34, pp. 185-194 (2000).
Grimaldo et al., "Very Late Antigen-1 Mediates Corneal Lymphangiogenesis", Investigative Ophthalmology & Visual Science, vol. 52, No. 7, pp. 4808-4812 (2011).
Ivy et al., "An overview of small-molecule inhibitors of VEGFR signaling", Nature Reviews, Clinical Oncology, vol. 6, pp. 569-579 (2009).
Neufeld et al., "Vascular endothelial growth factor (Vegf) and its receptors", the Faseb Journal, vol. 13, pp. 9-22 (1999).
Robinson et al., "The protein tyrosine kinase family of the human genome", Oncogene, vol. 19, pp. 5548-5557 (2000).
Shimaoka et al., "Therapeutic Antagonists and Conformational Regulation of Integrin Function", Nature Reviews, Drug Discovery, vol. 2, p. 703-716 (2003).
Spinger, Timothy A., "Adhesion receptors of the immune system", Nature, vol. 346, pp. 425-434 (1990).
Veikkola et al., "Regulation of Angiogenesis via Vascular Endothelial Growth Factor Receptors", Cancer Research, vol. 60, pp. 203-212 (2000).
Yuen et al., "Combined Blockade of VEGFR-2 and VEGFR-3 Inhibits Inflammatory Lymphangiogenesis in Early and Middle Stages", Investigative Ophthalmology & Visual Science, vol. 52, No. 5, pp. 2593-2597 (2011).
Zhang et al., "Combined Blockade of VEGFR-3 and VLA-1 Markedly Promotes High-Risk Corneal Transplant Survival", Investigative Ophthalmology & Visual Science, vol. 52, No. 9, pp. 6529-6535 (2011).
Zhang et al., "Spontaneous Lymphatic Vessel Formation and Regression in the Murine Cornea", Investigative Ophthalmology & Visual Science, vol. 52, No. 1, pp. 334-338 (2011).

* cited by examiner

*Primary Examiner* — Phuong Huynh
(74) *Attorney, Agent, or Firm* — Glenn J. Foulds; Bret E. Field; Bozicevic, Field & Francis LLP

(57) ABSTRACT

Methods of modulating the occurrence of lymphangiogenesis in a subject are provided. In some instances, the method is a method of treating transplant rejection in the subject. Aspects of the methods include administering to the subject an effective amount of: a first antagonist for a tyrosine kinase receptor and a second antagonist for an integrin receptor. In some embodiments, the methods include enhancing survival of transplanted tissue in a subject. Aspects of the invention further include compositions, e.g., pharmaceutical compositions and kits that find use in methods of the invention.

22 Claims, 5 Drawing Sheets

METHODS AND COMPOSITIONS FOR MODULATING LYMPHANGIOGENESIS, E.G., TO TREAT TRANSPLANT REJECTION, IN A SUBJECT

CROSS-REFERENCE TO RELATED APPLICATIONS

This application claims the benefit of U.S. Provisional Patent Application No. 61/683,635, filed Aug. 15, 2012, which application is incorporated herein by reference in its entirety.

STATEMENT REGARDING FEDERALLY SPONSORED RESEARCH

This invention was made with government support under Grant No. NIH EY017392 awarded by the National Institutes of Health, and Grant No. W81XWH-07-0017 awarded by the Department of Defense. The government has certain rights in the invention.

INTRODUCTION

Lymphangiogenesis is involved in a number of diseases, such as cancer metastasis, inflammatory and immune diseases. For example, one reason for transplant failure is immune-mediated rejection. Transplantation can restore the functions of a tissue or an organ to patients when other treatments have failed or the patients are experiencing medical emergencies. Corneal transplantation is an example of a tissue or solid organ transplantation. Patients who are blind as a result of corneal diseases after traumatic, inflammatory, infectious, or chemical injuries tend to have inflamed and vascularized corneas and experience a transplant rejection rate which can be as high as 90%.

SUMMARY

Methods of modulating the occurrence of lymphangiogenesis in a subject are provided. In some instances, the method is a method of treating transplant rejection in the subject. Aspects of the methods include administering to the subject an effective amount of a first antagonist for a tyrosine kinase receptor; and an effective amount of a second antagonist for an integrin receptor. In some embodiments, the methods include enhancing survival of transplanted tissue in a subject. Aspects of the method further include transplanting tissue in a graft bed of the subject. In some embodiments, the graft bed is inflamed and vascularized, and administering the first and second antagonists selectively inhibits lymphatic vessels. Aspects of the invention further include compositions, e.g., pharmaceutical compositions and kits, etc., that find use in methods of the invention.

In some embodiments, the tyrosine kinase receptor is a VEGFR. In certain embodiments, the tyrosine kinase receptor is VEGFR-3.

In some cases, the first antagonist comprises a first specific binding member that specifically binds to the tyrosine kinase receptor. In certain embodiments, the specific binding member is an antibody or binding fragment thereof. In some instances, the antibody or binding fragment thereof specifically binds to a VEGFR. In certain instances, the antibody or binding fragment thereof specifically binds to VEGFR-3.

In some embodiments, the integrin receptor is a VLA. In certain embodiments, the integrin receptor is VLA-1.

In some instances, the second antagonist comprises a second specific binding member that specifically binds to the integrin receptor. In certain embodiments, the specific binding member is an antibody or binding fragment thereof. In some instances, the antibody or binding fragment thereof specifically binds to a VLA. In certain embodiments, the antibody or binding fragment thereof specifically binds to VLA-1.

Transplant rejection may include rejection of material such as a tissue or an organ. In some instances, the method includes treating rejection of transplanted tissue. In some embodiments, the method includes treating rejection of a transplanted organ, e.g., a solid organ.

In some cases, the method further includes transplanting tissue in a graft bed of the subject, where the administering is performed prior to the transplanting. In some instances, the administering is performed during or after the transplanting.

In some embodiments, the graft bed of the subject is inflamed and vascularized and the method includes reducing inflammatory lymphangiogenesis in the graft bed.

In certain embodiments, the graft bed of the subject is uninflamed and avascular and the method includes preventing lymphangiogenesis in the graft bed.

In some embodiments, the first and second antagonists are administered simultaneously. In other embodiments, the first and second antagonists are administered sequentially.

In some instances, the method involves a transplanted organ. In some cases, the organ is a heart, a kidney or a lung organ. In certain instances, the method involves a transplanted tissue. In certain cases, the tissue is a skin or an ocular tissue. In certain instances, the transplanted tissue includes ocular tissue. In certain embodiments, the ocular tissue includes corneal tissue.

In certain cases, the method includes reducing lymphangiogenesis of the corneal tissue. In some instances, the method includes reducing the occurrence of opacity of the corneal tissue. In some embodiments, the method does not significantly inhibit blood vessel function in the tissue. In some instances, the method includes inhibiting lymphatic vessel function in the tissue. In certain instances, the method includes reducing lymphangiogenesis around the grafting border between the transplanted tissue and the graft bed.

In certain instances, the method includes inhibiting lymphatic vessel growth in the tissue. In some cases, the subject is a mammal. In some instances, the mammal is a mouse. In other instances, the mammal is a human.

Also provided are pharmaceutical compositions comprising a first antagonist for a tyrosine kinase receptor; and a second antagonist for an integrin receptor. In some cases, the composition further comprises a pharmaceutically acceptable solution.

Also provided are kits comprising a sterile container containing a pharmaceutically acceptable solution comprising a first antagonist for a tyrosine kinase receptor and a second antagonist for an integrin receptor; and a sealed package configured to maintain the sterility of the sterile container.

DETAILED DESCRIPTION

Figure 1:
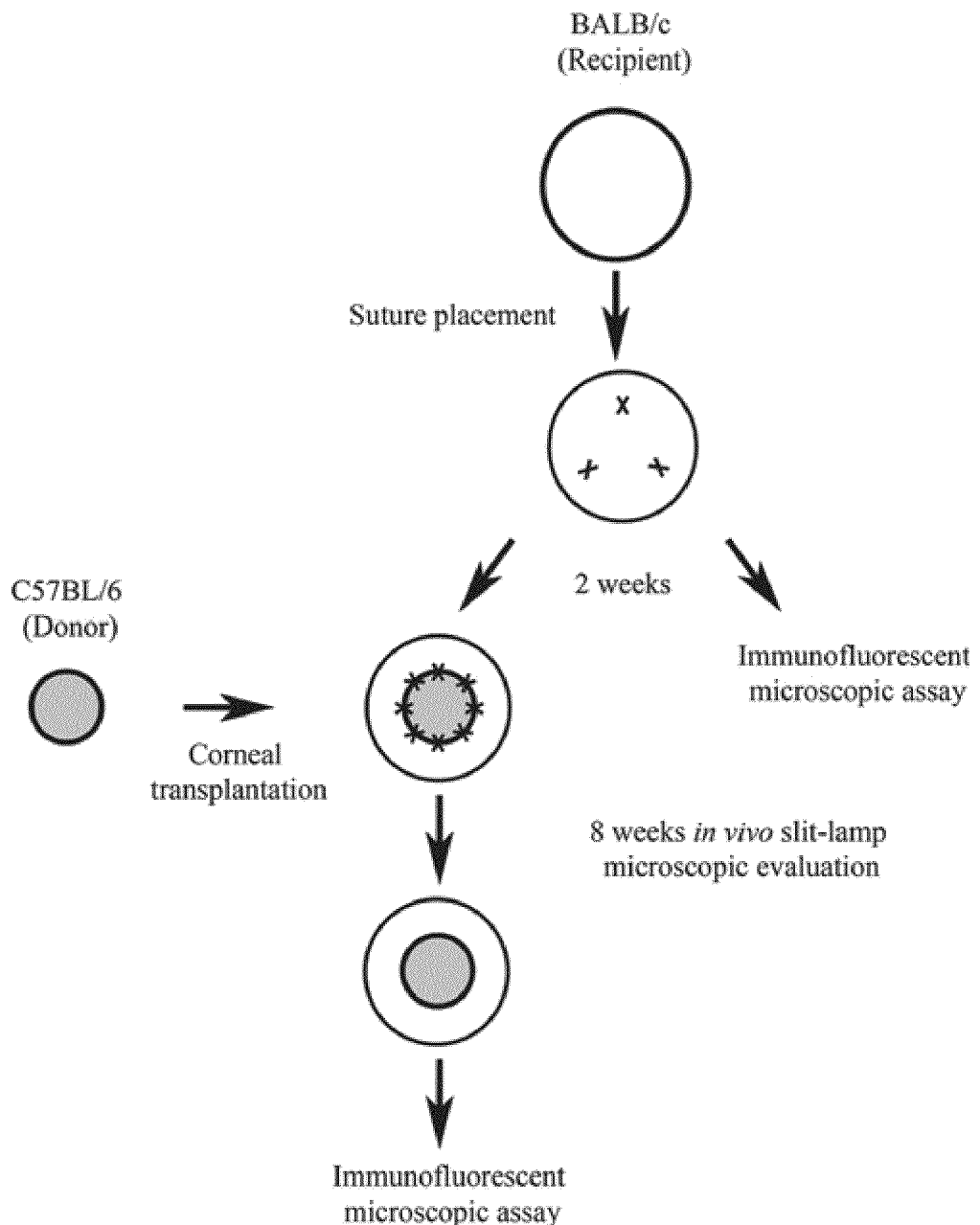
FIG. 1 shows a schematic diagram demonstrating general experimental methods of interest. Normal BALB/c mice are subjected to corneal suture placement to induce high-risk host beds. Corneal transplantations are performed between normal C57BL/6 (donor) and inflamed BALB/c (recipient) mice. Mice are observed and evaluated by ophthalmic slit-lamp microscopy and immunofluorescent microscopic assays are performed to investigate blood and lymphatic vessels.

As summarized above, aspects of the invention include methods of modulating the occurrence of lymphangiogenesis in a subject. Aspects of the methods include administering to the subject an effective amount of a first antagonist for a tyrosine kinase receptor; and an effective amount of a second antagonist for an integrin receptor. As such, the first and second antagonists are administered in combination. The methods and compositions may be used to treat a subject for a lymphatic-related disease such as inflammation.

In some instances, the methods include enhancing survival of a transplanted organ in a subject. In some embodiments, the methods include enhancing survival of transplanted tissue in a subject. Aspects of the methods further include transplanting tissue in a graft bed of the subject. In some embodiments, the graft bed is inflamed and vascularized when the tissue is transplanted to the graft bed, and administering the first and second antagonists enhances survival of transplanted tissue in the subject.

Aspects of the invention further include compositions, e.g., pharmaceutical compositions and kits, etc., that find use in methods of the invention. Embodiments of the present disclosure find use in a variety of different applications, including research and therapeutic applications.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits, ranges excluding either or both of those included limits are also included in embodiments of the present disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods of modulating the occurrence of lymphangiogenesis in a subject. As used herein, the term "lymphangiogenesis" refers to the growth of new lymphatic vessels. Lymphangiogenesis may occur at a variety of sites in the subject. Lymphangiogenesis may be involved in a variety of pathological or disease conditions including neoplasm metastasis, oedema, rheumatoid arthritis, psoriasis, lymphangiomatosis and impaired wound healing. In some cases, lymphangiogenesis is inflammatory. In some cases, modulating the occurrence of lymphangiogenesis means the growth of new lymphatic vessels is at least ameliorated. As used herein, amelioration is used in a broad sense to refer to at least a reduction in the magnitude of a parameter, e.g. symptom, associated with the condition being targeted.

In some instances, modulating the occurrence of lymphangiogenesis is meant to encompass the amelioration of one or more functions of lymphatic vessels (LV) associated with a pathologic or disease condition. In certain embodiments, the one or more functions of lymphatic vessels which are at least ameliorated include, but are not limited to, transport of lymph through the vessels, transport of any convenient components of the lymphatic system (e.g., antigens and/or antigen-presenting cells) through the afferent pathway, draining of lymph nodes; infiltrations of macrophages, leukocytes, or T cells; and acting as reservoir for lymphatic system components (e.g., as described herein). Such functions of the lymphatic vessels may be measured using any convenient bioassay, or in vivo.

In certain cases, the parameter of interest, e.g., growth and/or function of lymphatic vessels, is reduced or inhibited by about 20% or more, such as by about 30% or more, about 40% or more, about 50% or more, about 60% or more, about 70% or more, about 80% or more, about 90% or more, or about 100% as compared to a suitable control, and as measured by a convenient bioassay, or in vivo.

In some instances, prior to the administrating step, lymphangiogenesis has occurred in the subject, and the method of modulating includes reducing lymphangiogenesis in the subject. In certain instances, lymphangiogenesis has not occurred in the subject prior to the administrating step, and the method of modulating includes preventing lymphangiogenesis from occurring. In such cases, the subject may be at risk of experiencing lymphangiogenesis, but this risk is reduced by practicing the subject methods. In some embodiments, modulating the occurrence of lymphangiogenesis means that lymphangiogenesis does not occur in the subject, e.g., lymphangiogenesis is prevented. In other words, practicing the subject method includes maintaining the tissue of the subject in a lymphatic-free or low state.

The methods of the present disclosure find use in the treatment of a variety of conditions associated with lymphangiogenesis. Pathology or disease conditions of interest include, but are not limited to, cancers, infections, inflammatory conditions, neoplasm metastasis, oedema, rheumatoid arthritis, psoriasis, lymphangiomatosis, impaired wound healing and transplant rejections. In some cases, the methods find use in treatment of patients in need of a transplant, including those patients at risk of transplant rejection. As such, in certain instances, the method further includes transplanting tissue in a graft bed of the subject. As such, in certain cases, the method further includes transplanting an organ into the subject.

In some embodiments, the method includes enhancing survival of the transplanted tissue in a subject. In some embodiments, the method includes enhancing survival of the transplanted organ in a subject. As used herein, by "enhancing survival" is meant an increase in transplant survival rate as measured at any convenient time post transplantation, using any convenient bioassay, or in vivo. In some instances, the survival rate is enhanced to a rate of about 20% or more, about 30% or more, about 30% or more, about 40% or more, about 50% or more, about 60% or more, about 70% or more, about 80% or more, about 90% or more, or about 100% as measured in a convenient bioassay, or in vivo, as compared to a suitable control. In some instances, where the transplanted tissue is ocular tissue, and the survival rate is measured at a convenient time 2 or more weeks post-transplantation, such as, at 3, 4, 5, 6, 7 or 8 weeks post-transplantation, the survival rate is enhanced to a rate of about 20% or more, such as by about 30% or more, about 40% or more, about 50% or more, about 60% or more, about 70% or more, about 80% or more, about 90% or more, or about 100% as measured in a convenient bioassay, or in vivo. In certain embodiments, the negative control survival rate of transplantation is about 50% or less, such as about 40% or less, about 30% or less, or 20% or less.

Prior to transplantation, the graft bed may be inflamed and vascularized, and administering the first and second antagonists can inhibit lymphatic vessel growth and/or function to reduce inflammatory lymphangiogenesis in the graft bed. In some embodiments, the graft bed is uninflamed and avascular and the method includes maintaining the graft bed as uninflamed and avascular before, during and/or after transplantation. Administration of the first and second antagonists may result in selective inhibition of the growth of and/or a function of the lymphatic vessels while having no significant effect on the growth of and/or a function of the blood vessels.

Practicing the subject methods may result in selective inhibition of the growth of lymphatic vessels of interest relative to the growth of blood vessels of interest. In certain embodiments, the subject methods may result in selective inhibition of one or more functions of the lymphatic vessels (e.g., as described herein) relative to one or more analogous functions of the blood vessels. By selective inhibition is meant the lymphatic vessels are inhibited to a greater extent than the blood vessels. In certain cases, blood vessel growth and/or function is not significantly inhibited (In certain cases, blood vessel growth and/or function is inhibited by about 20% or less, such as 10% or less, or 5% or less. In certain cases, lymphatic vessel growth and/or function is inhibited in the corneal tissue. It is understood that the selection of lymphatic and blood vessels of interest for determining selective inhibition is dependent on a number of factors, such as the type of tissue involved, the type of pathologic insult to the tissue, the site and location of a graft bed, and the site of administration, which factors may be readily determined.

In some cases, the lymphatic vessels are inhibited (e.g., lymphatic vessel growth and/or function) by about 30% or more, while the blood vessels are inhibited (e.g., blood vessel growth and/or function) by about 30% or less. In certain instances, the lymphatic vessels are inhibited by about 30% or more, such as about 40% or more, about 50% or more, about 60% or more, about 70% or more, about 80% or more, about 90% or more, or about 100% as measured by any convenient bioassay, or in vivo. In certain embodiments, the blood vessels are inhibited by about 70% or less, such as about 60% or less, about 50% or less, about 40% or less, about 30% or less, about 20% or less, about 10% or less, about 5% or less, or does not inhibit at all. All of the above values are presented in terms of a suitable control.

In some cases, the method modulates lymphangiogenesis of the corneal tissue. In certain embodiments, inflammatory lymphangiogenesis of the corneal tissue is eliminated, e.g., the tissue is transformed from an inflamed lymphangeneic state to an uninflamed lymphatic-reduced state. In some embodiments, the untreated corneal tissue is inflamed and vascularized, and after treatment according to the subject methods the tissue is reduced in inflammation and vascularity, as measured in a convenient bioassay, or in vivo. In certain cases, after treatment, the tissue is uninflamed and/or avascular. In some instances, practicing the subject method reduces the occurrence of opacity of the corneal tissue. In some embodiments, the opacity of the corneal tissue is reduced by about 20% or more, such as about 30% or more, about 40% or more, about 50% or more, about 60% or more, about 70% or more, about 80% or more, about 90% or more, or about 100%, as measured in a convenient bioassay, or in vivo, at a convenient time post-transplantation, e.g., 2 or more weeks, such as 3, 4, 5, 6, 7 or 8 weeks post-transplantation, as compared to a suitable control.

As used herein, the term "effective amount" refers to that amount of a substance (e.g., an antagonist of interest) that produces some desired local or systemic effect. Effective amounts of first and second antagonists of interest vary depending on a variety of factors including, but not limited to, the weight and age of the subject, the condition being treated, the severity of the condition, the manner of administration and the like, and can readily be determined, e.g., determined empirically using data such as that data provided in the experimental section below.

In some instances, administration of an effective amount of a first antagonist for a tyrosine kinase receptor inhibits the activity of the tyrosine kinase receptor by about 20% or more, such as about 25% or more, about 30% or more, about 35% or more, 40% or more, about 45% or more, about 50% or more, about 55% or more, about 60% or more, about 65% or more, about 70% or more, about 75% or more, about 80% or more, about 85% or more, about 90% or more, about 95% or more, or about 100% in a convenient bioassay for tyrosine kinase receptor inhibition, or in vivo when used in an effective dose.

In some instances, administration of an effective amount of a second antagonist for an integrin receptor inhibits the activity of the integrin receptor by about 20% or more, such as about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100% in a convenient bioassay for integrin receptor inhibition, or in vivo when used in an effective dose.

Antagonists

As summarized above, aspects of the methods include the use of a first antagonist for a tyrosine kinase receptor in combination with a second antagonist for an integrin receptor. Any convenient tyrosine kinase receptors and integrin receptors may be targeted in practicing the subject methods. Tyrosine kinase receptors of interest and integrin receptors of interest are described in greater detail below.

As used herein, the term "antagonist" refers to any agent that blocks or reduces a biological activity mediated by a receptor of interest. In some cases, the antagonist blocks a biological response of the receptor that is mediated by a receptor agonist. In other words, the antagonist reduces or inhibits the activation of the receptor by the agonist. The antagonist may act directly or indirectly. The antagonist may act directly by disrupting the binding of an agonist to the active site of the receptor. The antagonist may mediate its blocking effect by binding to the active site of the receptor, or to an allosteric site of the receptor, or to any other convenient site of the receptor. In some embodiments, the antagonist is an inhibitor that competes with one or more endogenous ligands or substrates of the receptor. In some embodiments, an antagonist is an agent that interferes with one or more receptor-ligand binding interactions. In certain cases, the antagonist inhibits receptor signal transduction. The antagonist may act indirectly via blocking the action of a co-factor involved in biological regulation of the receptor's activity. The antagonist may act indirectly by blocking or inhibiting expression of the receptor, or an endogenous ligand or substrate thereof. Antagonist activity may be reversible or irreversible.

Any convenient agents may be utilized as an antagonist of a receptor of interest in the subject methods and compositions. Agents of interest include, but are not limited to, a receptor ligand, a receptor substrate, a receptor-binding antibody, a scaffolded protein binder, a nucleic acid, a small molecule, and a peptide; or a fragment, variant, or derivative thereof; or combinations of any of the foregoing.

Antibodies that may be used as antagonists in connection with the present disclosure can encompass, but are not limited to, monoclonal antibodies, polyclonal antibodies, bispecific antibodies, Fab antibody fragments, F(ab)$_2$ antibody fragments, Fv antibody fragments (e.g., $V_H$ or $V_L$), single chain Fv antibody fragments and dsFv antibody fragments. Furthermore, the antibody molecules may be fully human antibodies, humanized antibodies, or chimeric antibodies. The antibodies that may be used in connection with the present disclosure can include any antibody variable region, mature or unprocessed, linked to any immunoglobulin constant region. Minor variations in the amino acid sequences of antibodies or immunoglobulin molecules are encompassed by the present disclosure, providing that the variations in the amino acid sequence maintain 75% or more, e.g., 80% or more, 90% or more, 95% or more, or 99% or more of the sequence. In particular, conservative amino acid replacements are contemplated. Conservative replacements are those that take place within a family of amino acids that are related in their side chains. Whether an amino acid change results in a functional peptide can be determined by assaying the specific activity of the polypeptide derivative.

In some instances, the antagonist is an antibody, a receptor-binding fragment or domain thereof, or a derivative thereof. The antibody may be used to decrease receptor activation in a tissue of interest. Non-limiting examples of such antibodies include antibodies directed against any suitable extracellular or intra-membrane epitope of the receptor; antibodies directed against any suitable extracellular or intra-membrane epitope receptor; and antibodies directed against a soluble receptor ligand or a receptor-ligand complex. Also encompassed are bi-specific antibodies, e.g., antibodies in which each of the two binding domains recognizes a different binding epitope. In some embodiments, antibodies include those that reduce the interaction between the receptor and one or more ligands. Such blocking antibodies may be identified using any convenient competition assays. In certain embodiments, the receptor specific antibody is configured to inhibit signal transduction of the receptor.

In some cases, the antagonist is a receptor ligand. Such ligands may include a structural modification relative to an endogenous receptor ligand or substrate that renders the ligands effective in inhibiting the receptor of interest. In certain cases, such receptor-binding antagonists are polypeptides, nucleic acids, small molecules, or an analog or derivative thereof.

In certain cases, the antagonist is a soluble polypeptide. A variety of soluble polypeptides may be used as antagonists of a receptor of interest. Such soluble polypeptide antagonists include, but are not limited to, a polypeptide that includes an extracellular domain of a receptor, or a convenient fragment thereof. Such soluble polypeptides may bind with high affinity to an endogenous ligand or substrate of the receptor. In certain embodiments, the soluble polypeptide comprises a globular domain of a receptor of interest. As used herein, soluble polypeptides include fragments, functional variants, and modified forms soluble polypeptides. These fragments, functional variants, and modified forms of soluble polypeptides may antagonize the function of the receptor. Isolated fragments of these soluble polypeptides can be obtained by screening polypeptides recombinantly produced from the corresponding fragment of the nucleic acid encoding the soluble polypeptide. In addition, fragments can be chemically synthesized using any convenient techniques, e.g., conventional Merrifield solid phase Fmoc or Boc chemistry. The fragments can be produced (recombinantly or by chemical synthesis) and tested to identify those peptidic fragments that can function to inhibit function of the receptor of interest. In certain embodiments, the antagonist is a functional variant of a soluble polypeptide comprising an amino acid sequence that is 80% or more, such as 85% or more, 90% or more, 95% or more, 97% or more, or 99% or more identical to an extracellular domain of the receptor of interest.

In some instances, the antagonist is a small molecule antagonist of the receptor of interest. Small molecules of interest include, but are not limited to, small organic or inorganic compounds having a molecular weight (MW) of more than 50 and less than about 2,500 daltons (Da), such as more than 50 and less than about 1000 Da, or more than 50 and less than about 500 Da. "Small molecules" encompasses numerous biological and chemical classes, including synthetic, semi-synthetic, or naturally-occurring inorganic or organic molecules, including synthetic, recombinant or naturally-occurring polypeptides and nucleic acids. Small molecules of interest may comprise functional groups necessary for structural interaction with proteins, particularly hydrogen bonding, and may include at least an amine, carbonyl, hydroxyl or carboxyl group, and may contain at least two of the functional chemical groups. The small molecules may comprise cyclical carbon or heterocyclic structures and/or aromatic or polyaromatic structures substituted with one or more of the above functional groups. Small molecules are also found among biomolecules including peptides, saccharides, fatty acids, steroids, purines, pyrimidines, derivatives, structural analogs or combinations thereof.

In some cases, the antagonist is an inhibitor of expression of the receptor or an endogenous receptor ligand or substrate thereof. Any convenient inhibitor of expression of a tyrosine kinase receptor of interest, an integrin receptor of interest, or an endogenous receptor ligand or substrate thereof may be utilized as an antagonist in the subject methods. Such antagonists may act to inhibit expression at a transcriptional, translational, or post-translational level. In some embodiments, the inhibitors are nucleic-acid based, including, without limitation, DNA, RNA, chimeric RNA/DNA, protein nucleic acid, and other nucleic acid derivatives. In some embodiments, the expression inhibitors encompass RNA molecules capable of inhibiting receptor production when introduced into a receptor-expressing cell (termed RNAi), including short hairpin double-stranded RNA (shRNA). In some instances, the expression inhibitors are small interfering RNA (siRNA). It will be understood that any sequence capable of reducing the cell surface expression of a receptor, or reducing the expression of a receptor ligand, may be used in practicing the methods of the present disclosure.

In some embodiments, the antagonist is a scaffolded polypeptide binder. A scaffold refers to an underlying peptidic framework (e.g., a consensus sequence or structural motif) from which a polypeptide agent arose. The underlying scaffold sequence includes those residues that are fixed and variant residues that may confer on the resulting polypeptide agents different functions, such as specific binding to a target receptor. Such structural motifs may be characterized and compared structurally as a combination of particular secondary and tertiary structural elements, or alternatively, as a comparable primary sequence of amino acid residues. Any convenient scaffolds and scaffolded polypeptides may be utilized as antagonists in the subject methods. In some embodiments, such antagonists may be identified utilizing a recombinant screening method such as phage display screening. Scaffolded polypeptide binders of interest include, but are not limited to, synthetic small proteins and recombinant small proteins such as Affibodies.

Target Tyrosine Kinase Receptors and Antagonists Thereof

As used herein, the terms "tyrosine kinase receptor", "receptor tyrosine kinase" and "receptor type protein tyrosine kinase" are used interchangeably and refer to the class of cellular receptors that have protein-tyrosine kinase activity. Any convenient tyrosine kinase receptors may be targeted for blocking in the subject methods. Tyrosine kinase receptors of interest include, but are not limited to, those receptor-type protein tyrosine kinases described by Robinson et al. ("The protein tyrosine kinase family of the human genome," Oncogene (2000) 19, 5548-5557), the disclosure of which is herein incorporated by reference in its entirety. In some instances, the tyrosine kinase receptor belongs to a receptor sub-family selected from the group consisting of ALK, AXL, DDR, EGFR, EPH, FGFR, INSR, MET, MUSK, PDGFR, PTK7, RET, ROR, ROS, RYK, TIE, TRK, VEGFR and AATYK, such as one of the human receptor tyrosine kinases described in Table 2b of Robinson et al. Oncogene (2000) 19, 5548-5557, the disclosure of which is herein incorporated by reference. In some embodiments, the tyrosine kinase receptor belongs to the VEGFR subfamily. Tyrosine kinase receptors of interest include, but are not limited to, the tyrosine kinase receptors described by Gerwins et al. (2000, Crit. Rev. Oncol. Hematol., 34, 185-194), Veikkola et al. (2000, Cancer Res., 60, 203-212) and Neufeld et al. (1999, FASEB J., 13, 9-22), the disclosures of which are herein incorporated by reference in their entirety.

In certain embodiments, the tyrosine kinase receptor is vascular endothelial growth factor receptor-3 (VEGFR-3). In certain embodiments, the tyrosine kinase receptor is vascular endothelial growth factor receptor-2 (VEGFR-2). In certain embodiments, the tyrosine kinase receptor is vascular endothelial growth factor receptor-1 (VEGFR-1).

Any convenient antagonist of a tyrosine kinase receptor of interest (e.g., as described herein) may be utilized in the subject methods. Tyrosine kinase receptor antagonists of interest include, but are not limited to, a tyrosine kinase receptor ligand or substrate; a soluble polypeptide tyrosine kinase receptor fragment, variant, or derivative thereof; an antibody, or a fragment, variant, or derivative thereof (such as a tyrosine kinase receptor binding antibody, e.g., a VEGFR-3 binding antibody); a nucleic acid (or variant or derivative thereof) that inhibits expression of a tyrosine kinase receptor, or a ligand thereof; a peptide or small molecule that blocks a tyrosine kinase receptor in a cell; peptides or small molecules that interfere with the formation or function of the tyrosine kinase receptor; peptides or small molecules that alter tyrosine kinase receptor signal transduction; and combinations of any of the foregoing.

In some embodiments, the tyrosine kinase receptor antagonist is a VEGFR-3 antagonist. In certain cases, the antagonist is a soluble polypeptide that inhibits a tyrosine kinase receptor, e.g., a VEGFR. A variety of soluble polypeptides may be used that inhibit the activity of a VEGFR receptor, including but not limited to, VEGFR-3 or VEGFR-2, and convenient fragments thereof (e.g., an extracellular domain or a globular domain). Such soluble polypeptides may bind with high affinity to a ligand such as, for example, VEGF-C, VEGF-D or VEGF-A.

In some instances, the tyrosine kinase receptor antagonist is a small molecule. In certain embodiments, the small molecule is a VEGFR inhibitor, such as a compound described by Ivy et al. ("An overview of small-molecule inhibitors of VEGFR signaling", Nature Reviews Clinical Oncology, 2009, October; 6(10):569-79), the disclosure of which is herein incorporated by reference in its entirety. Small molecule VEGFR inhibitors of interest include, but are not limited to, AEE788, axitinib, motesanib, cediranib, vandetanib, sorafenib, telatinib, BIBF-1120, brivanib alaninate, dovitinib lactate, CP-547,632, pazopanib, OSI-930, OSI99, vatalanib, semaxinib, SU6668, and sunitinib, as described in Table 1 of Ivy et al. In certain embodiments, the antagonist is a quinazoline small molecule inhibitor of a VEGFR, or a pyrazolo-pyrrolo-pyridopyrimidine small molecule inhibitor of a VEGFR e.g., as described by Klohs et al., ("Inhibitors of tyrosine kinase." Curr. Opin. Oncol. 9, 562-568 (1997)) or Lawrence & Niu ("Protein kinase inhibitors: the tyrosine-specific protein kinases." Pharmacol. Ther. 77, 81-114 (1998)).

In certain embodiments, the antagonist is an antagonist of vascular endothelial growth factor receptor-3 (VEGFR-3). Any convenient antagonists of VEGFR-3 may be utilized in the subject methods. VEGFR-3 antagonists of interest include, but are not limited to, anti-VEGFR-3 antibodies (e.g., as described herein). In some instances, the VEGFR-3 antagonist comprises a first specific binding member that specifically binds to the VEGFR-3 receptor. In certain cases, the specific binding member is an antibody or binding fragment thereof. In some embodiments, the antibody or binding fragment thereof specifically binds to VEGFR-3.

Target Integrin Receptors and Antagonists Thereof

As used herein, the term "integrin receptor" refers to the integrin family of adhesion receptors. Any convenient integrin receptors may be targeted for blocking in the subject methods. Integrin receptors of interest include, but are not limited to, those described by Springer ("Adhesion receptors of the immune system," Nature, 1990, 346, 425-434) and Shimaoka and Springer (2003, Nat. Rev. Drug Discov. 2, 703-716), the disclosures of which are herein incorporated by reference in their entirety. In some instances, the integrin receptor belongs to the β1 (CD29) subfamily of integrin receptors. In other instances, the integrin receptor belongs to the β2 (CD18) subfamily of integrin receptors. In yet other instances, the integrin receptor belongs to the β3 (CD61) subfamily of integrin receptors. In certain cases, the integrin receptor is selected from the group consisting of CD11a/CD18, LFA-1, CD11b/CD18, Mac-1, CR3, CD11c/CD18, p150, 95, CD-/CD29, VLA-1, CD49b/CD29, VLA-2, gpIaIIa, ECMRII, CD-/CD29, VLA-3, ECMRI, CD49d/CD29, VLA-4, LPAM-1, CD-/CD29, VLA-5, FNR, gpIc/IIa, ECMRVI, CD49f/C29, VLA-6, gpIc/IIa, CD49d/CD-, LPAM-2, CD49f/CD-, aE/34, CD41/CD61, gpIIbIIIa, CD51/CD61, VNR, CD51/CD29, CD51/CD- and aVβS, as described by Springer (Nature, 1990, 346, 425-434) in Table 1, the disclosure of which is herein incorporated by reference.

In some cases, the integrin receptor is a VLA ("very late antigen" or "very late activation antigen"). Any convenient VLA may be targeted for blocking in the subject methods. VLA integrin receptors of interest include, but are not limited to, VLA-1, VLA-2, VLA-3, VLA-4, VLA-5 and VLA-9. In some instances, the integrin receptor is VLA-1, also known as integrin α1β1. In other instances, the integrin receptor is VLA-2. In some embodiments, the integrin receptor is VLA-3. In certain embodiments, the integrin receptor is VLA-4. In certain cases, the integrin receptor is VLA-5. In certain cases, the integrin receptor is integrin α9β1 (VLA-9).

Any convenient antagonist of an integrin receptor of interest (e.g., as described herein) may be utilized in the subject methods. Integrin receptor antagonists of interest include, but are not limited to, an integrin receptor ligand or substrate, a soluble polypeptide integrin receptor fragment, variant, or derivative thereof; an antibody, or a fragment, variant, or derivative thereof (such as an integrin receptor binding antibody, e.g., a VLA-1 binding antibody); a nucleic acid (or variant or derivative thereof) that inhibits expression of an integrin receptor, or a ligand thereof; a peptide or a small molecule that blocks the integrin receptor in a cell; peptides or small molecules that interfere with the formation or function of the integrin receptor; peptides or small molecules that alter integrin receptor signal transduction; and combinations of any of the foregoing.

In some embodiments, the integrin receptor antagonist is a VLA-1 antagonist.

In some instances, the integrin receptor antagonist is a compound as described in WO2005019177 or WO 2005016883, the disclosures of which are herein incorporated by reference in their entirety.

In some embodiments, the integrin receptor antagonist is a VLA-1 inhibitor selected from an aminopiperidine amide compound, an N-biaryl isonipecotamide, a diaminopropionic acid derivative and a hydantoin compound, such as one of the VLA1 integrin inhibitors described by Thomas et al., Array Biopharma (www.arraybiopharma.com/_documents/Publication/). In certain instances, the integrin receptor antagonist is a compound as described in FIG. 8 of Shimaoka and Springer (2003, Nat. Rev. Drug Discov. 2, 703-716), the disclosure of which is herein incorporated by reference in its entirety, such as a compound selected from epifibatide, tirofiban, SB-265123, BIRT0377, LFA703, and A-286982.

In certain embodiments, the antagonist is an antagonist of a VLA protein. In certain instances, the antagonist is an antagonist of VLA-1. Any convenient antagonists of VLA-1 may be utilized in the subject methods. In some instances, the VLA-1 antagonist comprises a first specific binding member that specifically binds to the VLA-1 receptor. In certain cases, the specific binding member is an antibody or binding fragment thereof. In some embodiments, the antibody or binding fragment thereof specifically binds to VLA-1.

Any convenient protocol for administering to the subject the first and second antagonists may be employed. The particular protocol that is employed may vary, e.g., depending on the site of administration and whether the antagonists are e.g., antibodies, proteins, peptides or small molecules. For in vivo protocols, any convenient administration protocol may be employed. Depending upon the identity and binding affinity of the antagonists, the response desired, the manner of administration, e.g. locally or systemic, intraocular, periocular, retrobulbar, intramuscular, intravenous, intraperitoneal, subcutaneous, subconjunctival, topical, eye drops, i.v. s.c., i.p., oral, and the like, the half-life, the number of cells or size of the graft bed or transplanted tissue, various protocols may be employed.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the host to be treated is one amenable to treatment using the parent drug. Accordingly, a variety of subjects may be amenable to treatment using the methods and compositions disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As used herein, the terms "host", "subject", and "patient" are used interchangeably.

In some instances, the subject is in need of a transplantation. In some cases, the subject may be characterized as having a high-risk of transplant rejection (e.g., the subject has a graft bed that is inflamed and vascularized). In some instances, the subject may be characterized as having a low-risk of transplant rejection (e.g., the subject has a graft bed that is uninflamed and avascular).

Also provided are in vitro methods including contacting a sample comprising cells of interest with a first antagonist for a tyrosine kinase receptor; and a second antagonist for an integrin receptor. Any convenient in vitro methods may be utilized. In some instances, the sample includes cells that are maintained in a suitable culture medium, and the first and second antagonists are introduced into the culture medium. The term "sample" as used herein relates to a material or mixture of materials, typically, although not necessarily, in fluid form, containing one or more components of interest.

The biological activity or response of a receptor of interest may be mediated in vitro, in vivo, and/or in any convenient tissue or organ of interest. Tissues of interest include those tissues where blocking of one, two, or even more integrin and/or tyrosine kinase receptors are of interest. In some embodiments, the tissue comprises heart, lung, kidney, skin or ocular tissue. In certain embodiments, the tissue comprises heart tissue. In certain instances, the tissue comprises lung tissue. In certain cases, the tissue comprises kidney tissue. In some embodiments, the tissue comprises ocular tissue. In some embodiments, the ocular tissue is corneal tissue. Organs of interest include those organs where blocking of one, two, or even more integrin and/or tyrosine kinase receptors are of interest. In some embodiments, the organ is a heart, a lung or a kidney.

As used herein, the term "tissue" refers to both transplanted tissue and graft bed tissue or any other tissue of a subject. In some instances, the tissue is a tissue that is transplanted in a subject (i.e., transplanted tissue), where the tissue may be foreign tissue or the subject's own tissue, e.g., heterologous, homologous, or isologous graft tissue. In other instances, the tissue is graft bed tissue of the subject. As used herein, the term "graft bed" refers to the site to which a graft or transplanted tissue is joined. In some embodiments of the methods, tissue includes transplanted tissue and/or associated secondary lymphoid tissue.

In some embodiments, the methods further include transplanting tissue in a graft bed of the subject. In some embodiments, the methods further include transplanting an organ into the subject. Any convenient methods of transplantation, including methods of preparing a graft bed and methods of transplanting an organ or tissue into the graft bed, may be adapted for use in the subject methods.

Administration of the subject compositions (e.g., as described herein) may be performed at any convenient time before, during and/or after a transplantation procedure. In some cases, the administration is performed prior to transplantation. In some instances, the administration is performed during the transplantation procedure. In some embodiments, the administration is performed after the transplantation procedure.

The first and second antagonists may be administered sequentially, simultaneously, or a combination thereof, as desired. As such, the first and second agents are administered in combination. In some instances, the first and second antagonists are administered simultaneously (together, at the same time) as a single composition or as separate compositions but at the same time. In some cases, the first and second antagonists are administered sequentially (e.g., administer one composition immediately after the other; or administer one composition and after a time period administer the other composition), starting with either the first antagonist or the second antagonist, as desired.

Utility

The methods, compositions and kits of the present disclosure, e.g., as described above, find use in a variety of applications. Applications of interest include, but are not limited to: research applications and therapeutic applications. Methods of the invention find use in a variety of different applications including any convenient application where modulation of the occurrence of lymphangiogenesis can be achieved by blocking the biological action of a tyrosine kinase receptor and an integrin receptor.

The methods and compositions find use in a variety of therapeutic applications. Therapeutic applications of interest include, but are not limited to, the treatment of lymphatic and/or immune related disease conditions, including neoplastic disease conditions (e.g., cancers), immune or autoimmune diseases, inflammatory diseases, traumas, chemical burns, infections, and tissue and organ transplant rejection. There are many other disorders that are associated with a dysregulation of lymphatic and/or immune abnormalities.

In the context of cancer, the term "treating" includes any or all of: reducing growth of a solid tumor, inhibiting replication of cancer cells, reducing overall tumor burden, and ameliorating one or more symptoms associated with a cancer.

The subject methods may be employed in the treatment of a variety of conditions where there is lymphangiogenesis. In certain embodiments, the lymphangiogenesis is inflammatory lymphangiogenesis. In such applications, an effective amount of a first antagonist for a receptor and an effective amount of a second antagonist for a receptor is administered to the subject in need thereof. Treatment is used broadly, to include at least amelioration in one or more of the symptoms of the disease, as well as a complete cessation thereof, as well as a reversal and/or complete removal of the disease condition, i.e., a cure.

In some embodiments, the subject methods are employed in the treatment of subjects in need of tissue transplantation (e.g., heart, lung, kidney, ocular, etc.). In such applications, an effective amount of a first antagonist for a tyrosine kinase receptor and an effective amount of a second antagonist for an integrin receptor is administered to the subject at any convenient time, before, during or after transplantation of the tissue. In such applications, the subject methods enhance survival of transplanted tissue in the subject.

The subject methods and compositions find use in a variety of transplantation applications, e.g., treatments to restore the functions of a tissue or an organ to patients whose other treatments have failed or who are experiencing medical emergencies. In some instances, the methods find use in treating or preventing immune-mediated rejection, which can reduce the risk of transplant failure. A variety of solid organ or tissue transplantation applications are envisaged, e.g., transplantation of tissues or organs where blood and lymphatic vessels are located, such as heart, kidney, lung, skin, eye, and the like.

In some embodiments, the methods and compositions find use in corneal transplantations. In certain embodiments, the corneal transplant patients have un-inflamed and avascular graft beds, which in some cases, can be characterized as low-risk of rejection. In certain instances, the corneal transplant patients have inflamed and highly vascularized corneas, which in some cases, can be characterized as having a high-risk of rejection, or as immune-compromised. In some cases, the subject methods prevent or treat lymphatic formation in the cornea after an inflammatory, traumatic, infectious, chemical, or toxic damage.

The subject methods find use in a variety of research applications. For example, the subject methods may be used to elucidate a synergistic relationship between the biological activities of two or more receptors of interest, e.g., synergistic relationships between a tyrosine kinase receptor of interest, and an integrin receptor of interest. The subject methods, compositions and kits may be used to screen for small molecule antagonists of a tyrosine kinase receptor of interest, and/or an integrin receptor of interest.

Formulations, Dosage and Administration

Antagonists for tyrosine kinase receptors, antagonists for integrin receptors, and combinations thereof (e.g., as described herein) find use in pharmaceutical compositions for modulating the occurrence of lymphangiogenesis in a subject, including methods of enhancing survival of transplanted tissue in a subject.

In some instances, the method further includes transplanting an organ into the subject. In some embodiments, the method further includes transplanting tissue in a graft bed of the subject. In some embodiments, the graft bed is inflamed and vascularized when the tissue is transplanted to the graft bed, and administering the first and second antagonists enhances survival of transplanted tissue in the subject.

In some cases, such treatment is achieved by administering to the subject an effective amount of a first antagonist for a tyrosine kinase receptor; and an effective amount of a second antagonist for an integrin receptor. For in vivo protocols, any convenient administration protocol may be employed. Depending upon the binding affinities of the antagonists, the response desired, the manner and site of administration, the half-life, the number of cells present, the type of target tissue, various protocols may be employed. The pharmaceutical compositions may be administered via any convenient method, such as but not limited to, parenterally, topically (e.g., by eye drops or transdermal patch), or orally. The number of administrations will depend upon the factors described above. The pharmaceutical compositions may be taken orally as a pill, powder, or dispersion; bucally; sublingually; injected intravascularly, intraperitoneally, intracranially subcutaneously; by inhalation, or the like. The precise dose and particular method of administration will vary and may be readily determined by the attending physician or human or animal healthcare provider, e.g., the dose and method may be determined empirically. The particular dosage of the first and/or second antagonists for any application may be determined in accordance with the procedures used for therapeutic dosage monitoring, where maintenance of a particular therapeutic level is desired over an extended period of time, for example, greater than about two weeks, or where there is repetitive therapy, with individual or repeated doses of the first and/or second antagonists over short periods of time, with extended intervals, for example, two weeks or more. A dose of the first and/or second antagonists within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the first and/or second antagonists are chronically administered, once the maintenance dosage of the first and/or second antagonists is determined, one could then do assays at extended intervals to be assured that the desired response was observed.

The first and/or second antagonists can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, liquids, or foams, containing, in addition to the active ingredient, such carriers as are appropriate. In some embodiments, the topical formulation is an eye drop liquid formulation for administration to the eye. Any convenient components may be included in the eye drop formulation. In some embodiments, the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (i.e., sunblocking agents), etc.

First and/or second antagonists (e.g., as described herein) that find use in the subject methods may be formulated for topical administration. The vehicle for topical application may be in one of various forms, e.g. a lotion, cream, gel, ointment, stick, spray, liquid eye drops, or paste. They may contain various types of carriers, including, but not limited to, solutions, aerosols, emulsions, gels, and liposomes. The carrier may be formulated, for example, as an emulsion, having an oil-in-water or water-in-oil base. Suitable hydrophobic (oily) components employed in emulsions include, for example, vegetable oils, animal fats and oils, synthetic hydrocarbons, and esters and alcohols thereof, including polyesters, as well as organopolysiloxane oils. Such emulsions also include an emulsifier and/or surfactant, e.g. a nonionic surfactant to disperse and suspend the discontinuous phase within the continuous phase.

Suppository formulations are also provided by mixing with a variety of bases such as emulsifying bases or water-soluble bases. Formulations suitable for vaginal administration may be presented as pessaries, tampons, creams, gels, pastes, foams. Pharmaceutical compositions of interest may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more antagonists. Similarly, unit dosage forms for injection or intravenous administration may include the antagonist(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of antagonist(s) calculated in an amount sufficient to produce the desired effect in association with a pharmaceutically acceptable diluent, carrier or vehicle. The specifications for the novel unit dosage forms of the present invention depend on the particular antagonist(s) employed and the effect to be achieved, and the pharmacodynamics associated with each antagonist in the host.

Dose levels can vary as a function of the specific antagonist, the nature of the delivery vehicle, and the like. Desired dosages for a given antagonist are readily determinable by a variety of means.

The dose administered to an animal, particularly a human, in the context of the present invention should be sufficient to effect a prophylactic or therapeutic response in the animal over a reasonable time frame, e.g., as described in greater detail below. Dosage will depend on a variety of factors including the strength of the particular antagonist(s) employed, the condition of the animal, and the body weight of the animal, as well as the severity of the illness and the stage of the disease. The size of the dose will also be determined by the existence, nature, and extent of any adverse side-effects that might accompany the administration of a particular antagonist(s).

In pharmaceutical dosage forms, the antagonist(s) may be administered in the form of a free base, their pharmaceutically acceptable salts, or they may also be used alone or in appropriate association, as well as in combination, with other pharmaceutically active compounds.

Kits

Aspects of the invention further include kits that find use in practicing the subject methods. In some embodiments, the kits for practicing the subject methods include one or more pharmaceutical formulations, which include a first antagonist for a tyrosine kinase receptor and a second antagonist for an integrin receptor. As such, in certain embodiments the kits may include a single pharmaceutical composition, present as one or more unit dosages, where the composition includes both the first antagonist for a tyrosine kinase receptor and a second antagonist for an integrin receptor. In other embodiments, the kits include two or more separate pharmaceutical compositions, each containing either a first antagonist for a tyrosine kinase receptor or a second antagonist for an integrin receptor.

Any of the components described herein may be provided in the kits, e.g., a first antagonist for a tyrosine kinase receptor, a second antagonist for an integrin receptor etc. A variety of components suitable for use in practicing the subject methods may find use in the subject kits. Kits may also include sterile containers, pharmaceutically acceptable solutions, freeze-dried solids thereof, tubes, buffers, etc., and instructions for use. The various components of the kits may be present in separate containers, or some or all of them may be pre-combined into a mixture in a single container, as desired.

In certain embodiments, the kit includes a sterile container containing a pharmaceutically acceptable solution comprising a first antagonist for a tyrosine kinase receptor and a second antagonist for an integrin receptor; and a sealed package configured to maintain the sterility of the sterile container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), hard drive etc., on which the information has been recorded. Yet another form of these instructions that may be present is a website address which may be used via the internet to access the information at a removed site. For example, a kit according to one embodiment includes as a first component (a) instructions for using a pharmaceutical composition, and as a second component (b) a pharmaceutical composition comprising the first antagonist, the second antagonist, or a combination thereof.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric Experimental General Methods The following general methods and materials may be adapted for use with any convenient antagonists, receptors and tissues in the subject methods.

Animals:

Six- to 8-week-old male C57BL/6 and BALB/c mice are used in all experiments. Mice are anesthetized using a mixture of ketamine, xylazine, and acepromazine (50 mg, 10 mg, and 1 mg/kg body weight, respectively) for each surgical procedure.

Induction of Corneal Neovascularization for Creation of High-Risk Host Beds:

High-risk host beds are created using methods similar to those described by Liu et al. ("Draining lymph nodes of corneal transplant hosts exhibit evidence for donor major histocompatibility complex (MHC) class II-positive dendritic cells derived from MHC class II-negative grafts. J Exp Med. 2002; 195: 259-268), Chen et al. ("Combined blockade of VEGFR-2 and VEGFR-3 inhibits inflammatory lymphangiogenesis in early and middle stages." Invest Ophthalmol Vis Sci. 2011; 52: 2593-2597), and Chen et al. ("Spontaneous lymphatic vessel formation and regression in the murine cornea", Invest Ophthalmol Vis Sci. 2011; 52:334-338). Briefly, three interrupted intrastromal sutures (11-0 nylon) are placed in the central cornea of the BALB/c mouse to induce inflammatory lymphangiogenesis and hemangiogenesis. All sutures are removed 2 weeks later, and the neovascularized corneas are used as high-risk host beds for corneal transplants.

Corneal Transplantation:

Corneal transplantation is performed in inflamed high-risk host beds using methods similar to those described by Chen et al. ("Vascular endothelial growth factor receptor-3 mediates induction of corneal alloimmunity", Nat Med. 2004; 10:813-815), Chen et al. ("Very late antigen 1 blockade markedly promotes survival of corneal allografts", Arch Ophthalmol. 2007; 125: 783-788), and Yamagami et al. ("Draining lymph nodes play an essential role in alloimmunity generated in response to high-risk corneal transplantation", Cornea. 2002; 21: 405-409). Briefly, the central cornea of the donor of C57BL/6 mice is marked with a 2-mm diameter microcurette and excised with Vannas scissors. The recipient graft bed is prepared by excising a circular 1.5-mm area in the central cornea. The donor button is placed onto the graft bed and secured with eight interrupted 11-0 nylon sutures (Sharpoint; Vanguard), followed by the application of antibiotic ointment.

In Vivo Assessment of Grafted Corneas:

All grafted eyes are first examined 3 days after surgery, and corneal sutures are removed on day 7. Corneal grafts are observed in vivo twice a week by ophthalmic slit-lamp biomicroscopy for 8 weeks and evaluated according to a grading scheme, similar to those described by Chen et al. ("Vascular endothelial growth factor receptor-3 mediates induction of corneal alloimmunity", Nat Med. 2004; 10:813-815) and Chen et al. ("Very late antigen 1 blockade markedly promotes survival of corneal allografts", Arch Ophthalmol. 2007; 125: 783-788). Briefly, the degree of opacification is graded between 0 (clear and compact graft) to 5+ (maximal corneal opacity with total obscuration of the anterior chamber). Grafts with an opacity score of 2+ or higher after 3 weeks or an opacity score of 3+ or higher at 2 weeks are regarded as rejected.

Pharmaceutical Interventions:

After surgery, mice are randomized to receive intraperitoneal administrations of either neutralizing antibodies of VEGFR-3 (700 μg) and VLA-1 (200 μg) or their isotype controls twice a week on the day of suture placement and thereafter. The treatment is given for 2 weeks and sutured corneas are sampled for analysis in immunofluorescent microscopic assays. The experiments are repeated twice with a total of 10 mice in each group. For transplantation, the treatment is given similarly up to 8 weeks after transplantation with a total of 10 mice in each group.

Immunofluorescence Microscopic Assay:

The experiments were performed according to protocols similar to those described by Chen et al. ("Very late antigen-1 mediates corneal lymphangiogenesis", Invest Ophthalmol Vis Sci. 2011; 52:4808-4812), Chen at al. ("Combined blockade of VEGFR-2 and VEGFR-3 inhibits inflammatory lymphangiogenesis in early and middle stages", Invest Ophthalmol Vis Sci. 2011; 52: 2593-2597), Chen et al. ("Spontaneous lymphatic vessel formation and regression in the murine cornea", Invest Ophthalmol Vis Sci. 2011; 52: 334-338) and Chen et al. ("Differential distribution of blood and lymphatic vessels in the murine cornea", Invest Ophthalmol Vis Sci. 2010; 51: 2436-2440). Briefly, fresh corneas are excised, fixed, and incubated with FITC-conjugated rat anti-mouse CD31 antibody or rat anti-mouse CD31/PECAM-1 followed by Alexa 488-conjugated donkey anti-rat IgG. These samples are then stained with rabbit anti-mouse LYVE-1, which was visualized by Cy3-conjugated donkey antirabbit IgG. The samples are mounted with mounting medium, observed with a fluorescence microscope, and photographed with a digital camera system. Vascular structures stained as $CD31^+LYVE$-

1⁻ are identified as blood vessels, whereas those stained as CD31⁺LYVE-1⁺ are defined as lymphatic vessels.

Vascular Quantification:

Vessels in whole-mount corneas are graded and analyzed using the ImageJ software, using methods similar to those described by Chen et al. (Invest Ophthalmol Vis Sci. 2011; 52: 4808-4812), Chen et al. (Invest Ophthalmol Vis Sci. 2011; 52: 2593-2597), Chen et al. (Invest Ophthalmol Vis Sci. 2011; 52: 334-338) and Chen et al. (Invest Ophthalmol Vis Sci. 2010; 51: 2436-2440). The blood or lymphatic vessel area is normalized to the total corneal area to obtain a percentage coverage score for each sample. Additionally, vessels in three different zones of the cornea after transplantation are also graded, using methods adapted from those described by Chen et al. (Arch Ophthalmol. 2007; 125:783-788), Dana et al. ("Loss and restoration of immune privilege in eyes with corneal neovascularization", Invest Ophthalmol Vis Sci. 1996; 37: 2485-2494), and Chen et al. ("Increased lymphangiogenesis and hemangiogenesis in infant cornea", Lymph Res Biol. 2011; 9: 109-114). Briefly, the quantification of vessels in the host beds or donor buttons is based on two primary parameters. One is the circumferential extent of 12 areas around the clock. A score of 1 is given to each area if the vessels are present in the sector. The other is the centripetal growth of the longest vascular frond in each area. A grade between 0 (no growth) and 2 (at the grafting border for host bed vessel quantification or at the center of the cornea for donor button vessel quantification) is given to each area. Scores for each area are then summed to derive the final index (range, 0-24; maximal score, 24=2×12). Vessels along the donor-graft borders are quantified based on their presence around 12 clocks (range, 0-12).

Statistical Analysis:

Results are expressed as the mean±SEM, and Student's t-tests are performed to evaluate the statistical significance of any difference between the control and treatment groups. Corneal graft survival is assessed by Kaplan-Meier survival curves. The association between the ingrowth of lymphatic vessels into each graft and its survival outcome is analyzed by the $X^2$ test. All statistical analysis is performed using statistical analysis software. P<0.05 is considered significant.

FIG. 1. Schematic diagram demonstrating general methods. Normal BALB/c mice are subjected to corneal suture placement to induce high-risk host beds. Two weeks later, sutures are removed and corneal transplantations are performed between normal C57BL/6 (donor) and inflamed BALB/c (recipient) mice. Mice are observed and evaluated in vivo twice a week by ophthalmic slit-lamp microscopic examination up to 8 weeks after transplantation. Immunofluorescence microscopic assays are performed to investigate blood and lymphatic vessels 2 weeks after suture placement and 8 weeks after corneal transplantation, respectively.

Results

Combined Blockade of VEGFR-3 and VLA-1 Selectively Inhibits Inflammatory Lymphangiogenesis in High-Risk Host Beds Lymphatic and blood vessels constitute the afferent and efferent pathways of the immune reflex arc of transplantation immunity. The effect of the combined blockade of VEGFR-3 and VLA-1 on the formation of new blood and lymphatic vessels in inflamed corneas was studied, which also served as recipient beds for high-risk transplantation. A suture placement model was used in the mouse cornea to induce significant ingrowth of both vessel types. The effect of VEGFR-3 and VLA-1 blockade was analyzed by comparing vascularized conditions in neutralizing antibody treatment and control groups. As shown in FIG. 2A (upper panels), though the combined blockade dramatically reduced inflammatory LG in the treatment group, little effect was demonstrated on blood vessels (FIG. 2A, lower panels), which was also confirmed by in vivo slit-lamp microscopic examination. Summarized data from repetitive experiments are presented in FIG. 2B (P<0.001).

Figure 2:
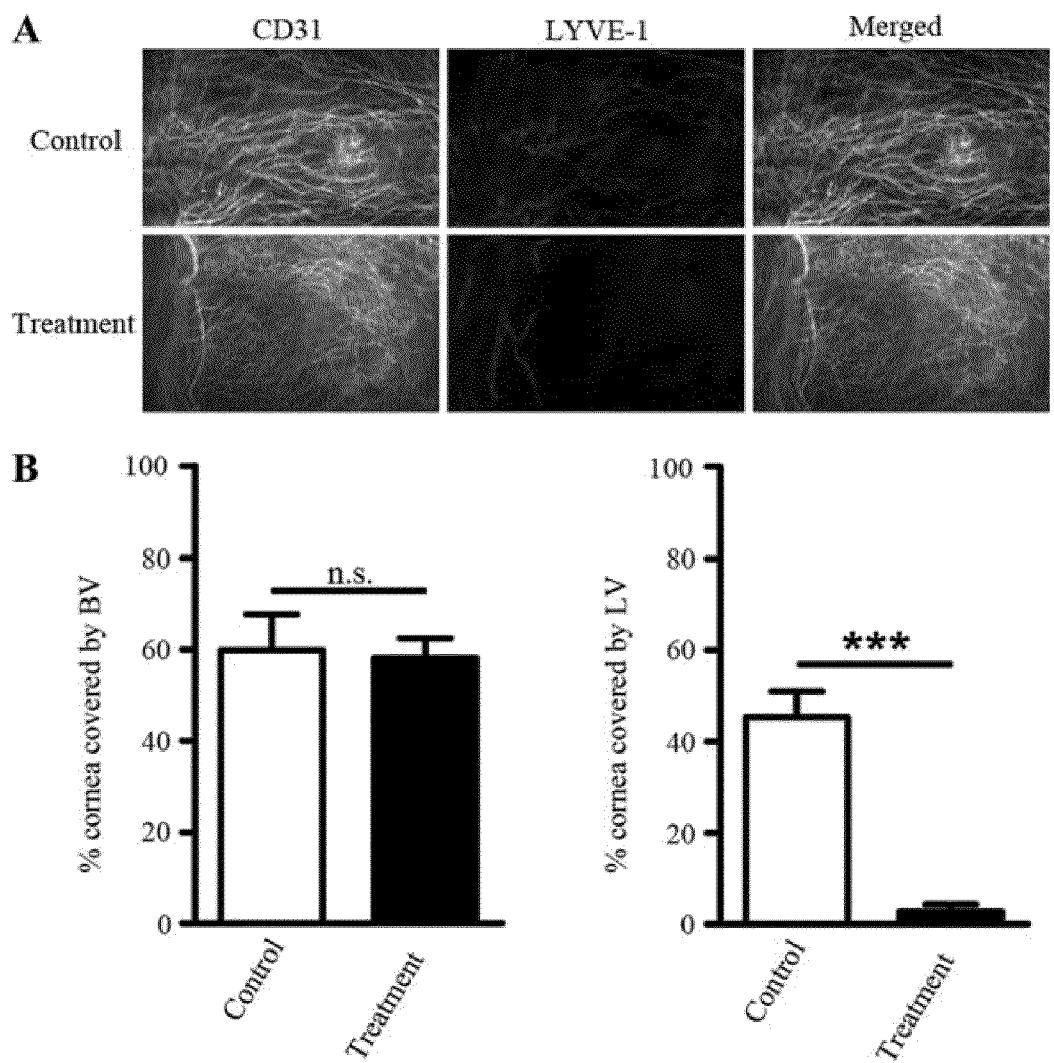
FIG. 2 illustrates selective inhibition of inflammatory lymphangiogenesis in mice host beds via treatment with antagonists of VEGFR-3 and VLA-1. (A) Representative wholemount micrographs and (B) summarized data showing significantly suppressed lymphangiogenesis but no significant change in blood vessels between groups (BV, blood vessels; LV, lymphatic vessels; ***$P<0.001$; n.s.: no significant difference).

FIG. 2. Combined blockade of VEGFR-3 and VLA-1 selectively inhibited inflammatory lymphangiogenesis (LG) in the host beds induced by suture placement. (A) Representative wholemount micrographs showing lymphangiogenesis after suture placement was significantly suppressed by the combined treatment. Blood vessels remained similar between the treatment and control groups. Green: CD31; red: LYVE-1. Original magnification, 100×. (B) Summarized data from repetitive experiments. BV, blood vessels; LV, lymphatic vessels. ***P<0.001. n.s.: no significant difference.

Combined Blockade of VEGFR-3 and VLA-1 Markedly Improves the Transparency of High-Risk Grafts High-risk transplantation was performed on the inflamed and highly vascularized host beds and the effect of the combined treatment on graft transparency was observed, an index for the outcomes of the transplants. Transplantation was performed between fully mismatched normal C57BL/6 (donor) and inflamed BALB/c (recipient) mice. All grafts in the treatment and control groups were evaluated in vivo twice a week by ophthalmic slit-lamp microscopy up to 8 weeks after transplantation. As demonstrated in FIGS. 3A and 3B, at all time points studied, the grafts in the treatment group showed greater clarity than those in the control group. Summarized data are presented in FIG. 3B (P 0.001).

Figure 3:
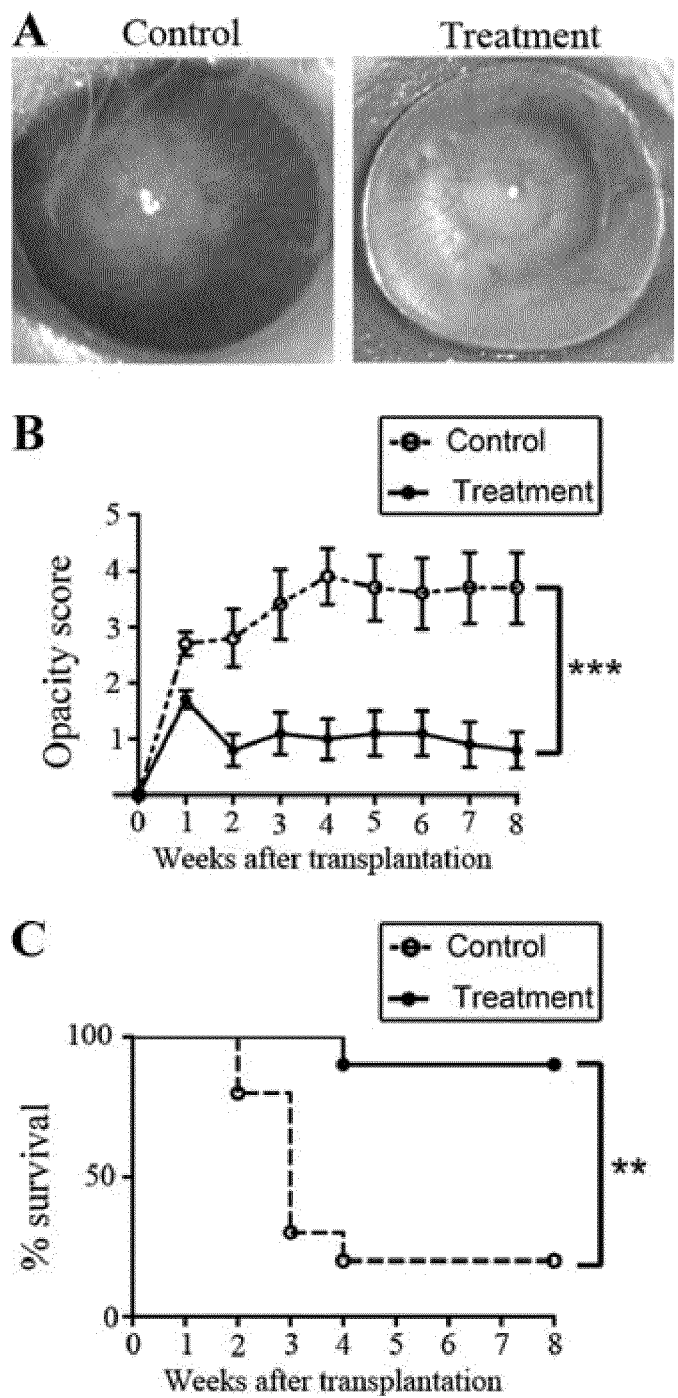
FIG. 3 illustrates the enhanced transplantation survival in high-risk grafts. (A) Slit-lamp images showing rejected and survived corneal grafts in control and treatment groups, respectively. (B) Graph showing treated grafts have lower opacity scores (*$P<0.001$). (C) Kaplan-Meier survival curves showing survival of treated grafts ($P<0.005$).

FIG. 3. Combined blockade of VEGFR-3 and VLA-1 blockade markedly promoted the outcomes of high-risk grafts. (A) Representative in vivo slit-lamp pictures showing rejected and survived corneal grafts in control and treatment groups 8 weeks after transplantation, respectively. (B) Summarized data showing grafts in the treatment group have lower opacity scores with greater clarity at all time points studied. *P<0.001. (C) Kaplan-Meier survival curves showing significantly higher rates of graft survival in the treatment group. P<0.005.

Combined Blockade of VEGFR-3 and VLA-1 Leads to Survival of High-Risk Transplants To further evaluate the effect of the combined treatment on high-risk transplant survival, all grafts in the treatment and control groups were evaluated for their survival rate twice a week up to 8 weeks after transplantation. The onset of high-risk corneal transplant rejection occurs around 2 to 3 weeks after surgery. As shown in FIG. 3C with Kaplan-Meier survival curves, the results showed a remarkable promotion of transplant survival by this treatment. It was observed that graft rejection in the control group started earlier, from 2 weeks after transplantation compared with 4 weeks in the treatment group. Within 3 weeks after transplantation, 70% of the grafts were already rejected in the control group, whereas all those in the treatment group survived. By 4 weeks after transplantation, only 20% of the grafts survived in the control condition. Grafts in the treatment condition showed a high survival rate of 90%, which remained until the end of the 8-week study (P<0.005). This treatment, therefore, suppressed both the onset and the scale of the rejection.

Combined Blockade of VEGFR-3 and VLA-1 Suppresses Lymphangiogenesis in Host Beds, Along Donor-Graft Borders, and into Donor Buttons The effect of combined treatment on the ingrowth of lymphatic or blood vessels into grafted corneas after high-risk transplantation was examined. Whole-mount intact corneas (including both host beds and donor buttons) from the treatment and control groups were collected by the end of the 8-week transplantation study and subjected to immunofluorescence microscopic assays using both anti-CD31 and anti-LYVE-1 antibodies. The effect of the combined treatment on lymphatic and blood vessels was analyzed in whole-mount corneas as well as three individual zones defined in grafted corneas. These included host beds, donor-graft borders and donor buttons, respectively (zone a-c, FIG. 4C). As shown in FIGS. 4A and 4B for whole corneal studies, lymphatic vessels in the treated corneas were significantly reduced (P<0.001), whereas no significant effect was observed for blood vessels.

Further analysis on the three different zones in the grafted corneas showed that while lymphatic vessels in the host beds were greatly suppressed by the treatment, those in the graft buttons or along the donor-graft borders were completely abolished (FIG. 4E; P<0.001). No significant differences were observed in all three areas for blood vessels (FIG. 4D).

Figure 4:
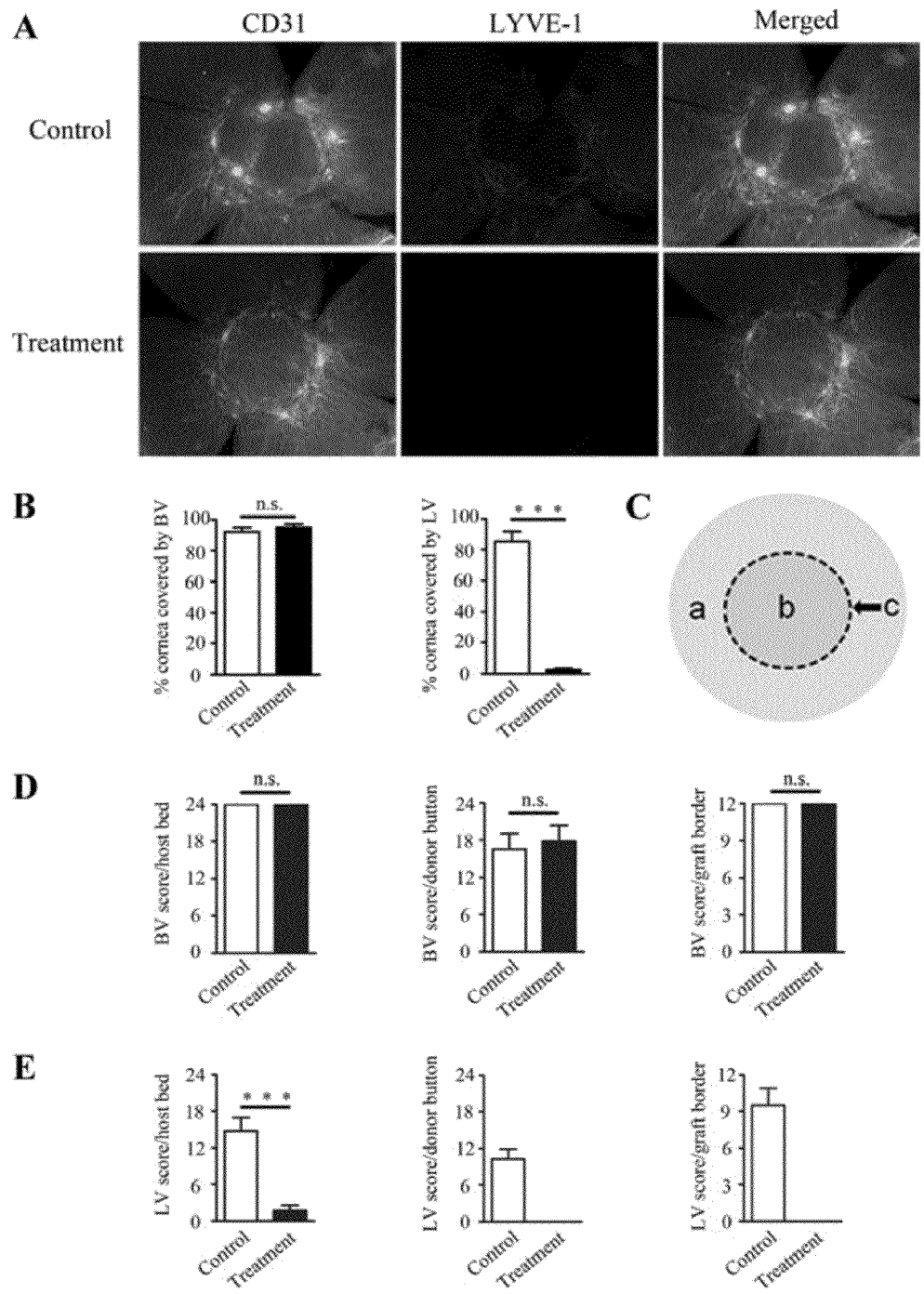
FIG. 4 illustrates selective inhibition of lymphangiogenesis in corneas after high-risk transplantation. (A) Wholemount micrographs showing suppression of lymphangiogenesis in treated grafted corneas, and no significant change in blood vessels between groups. (B) Summarized data for whole cornea assays (*$P<0.001$). (C) Schematic diagram of three zones analyzed on corneal vessels (zone a, host bed; zone b, donor button; zone c, donor graft border). (D) Data showing no significant difference on blood vessels in all three zones analyzed between the treatment and control groups. (E) Summarized data showing that lymphangiogenesis is blocked in three zones. By, blood vessels; LV, lymphatic vessels; n.s., no significant difference; *$P<0.001$.

FIG. 4. Combined blockade of VEGFR-3 and VLA-1 selectively inhibited lymphangiogenesis in the corneas after high-risk transplantation. (A) Representative whole-mount micrographs showing lymphangiogenesis in grafted corneas was significantly suppressed in the treatment group. Blood vessels were not affected. Green: CD31; red: LIVE-1. Original magnification, 50×. (B) Summarized data for whole cornea assays. *P<0.001. (C) Schematic diagram demonstrating three individual zones analyzed on corneal vessels after transplantation. Gray: zone a, host bed; blue: zone b, donor button; dotted line, arrow: zone c, donorgraft border. (D) Summarized data showing no significant difference on blood vessels in all three zones analyzed between the treatment and control groups. (E) Summarized data showing that while lymphangiogenesis was significantly suppressed by the treatment in host beds, it was completely eliminated along the grafting borders and in donor buttons. BV, blood vessels; LV, lymphatic vessels; n.s., no significant difference. *P<0.001.

Lymphangiogenesis Crossing the Donor-Graft Border Correlates with High-Risk Transplant Rejection Each cornea in the treatment and control groups was examined and the transplant outcome compared with the degree of lymphatic or blood vessel invasion in each sample. It was found that corneal grafts with few (FIG. 5A) or no lymphatic vessels (FIG. 5C) were more likely to survive in both treatment and control groups. In clear contrast, those grafts with significant lymphatic invasion were rejected (FIG. 5B). An association analysis between the degree of LG and graft rejection was performed. The grafts with severe LG reaching the donor-graft borders were rejected while those not affected by this high degree of LG survived. A strong correlation between these two parameters was, therefore, shown for high-risk transplantation, as summarized in FIG. 5D (P<0.005).

Figure 5:
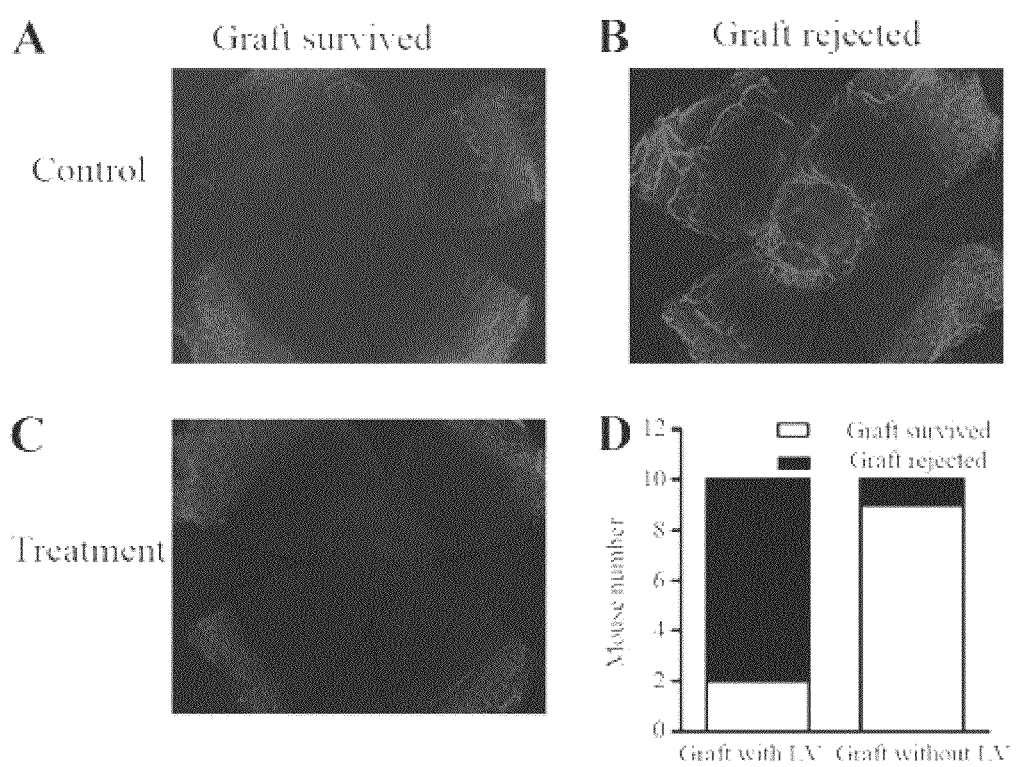
FIG. 5 illustrates lymphangiogenesis reaching the grafting border is highly associated with high-risk transplant rejection. (A-C) Whole-mount micrographs showing a survived graft with few lymphatic vessels in the control group (A), a rejected graft with significant lymphatic ingrowth across the donor-recipient border in the control group (B), and a survived graft without lymphatic invasion in the treatment group (C). (D) Data showing significant association between high degree lymphangiogenesis and transplant rejection. LV, lymphatic vessels. **$P<0.005$.

FIG. 5. Lymphangiogenesis reaching the grafting border was highly associated with high-risk transplant rejection. (A-C) Representative whole-mount micrographs showing a survived graft with few lymphatic vessels in the control group (A), a rejected graft with significant lymphatic ingrowth across the donor-recipient border in the control group (B), and a survived graft without lymphatic invasion in the treatment group (C). Red: LYVE-1. Original magnification, 25×. (D) Summarized data showing significant association between high degree lymphangiogenesis and transplant rejection. LV, lymphatic vessels. **P<0.005.

Summary:

High-risk corneal transplantation was performed between normal C57BL/6 (donor) and inflamed BALB/c (recipient) mice. The recipients were randomized to receive intraperitoneal injections of VEGFR-3 and VLA-1—neutralizing antibodies or their controls twice a week for up to 8 weeks after transplantation. Corneal grafts were evaluated by ophthalmic slit-lamp biomicroscopy and analyzed by Kaplan-Meier survival curve. Additionally, whole-mount corneas before and after transplantation were examined by immunofluorescent microscopic assays, and the correlation between lymphatic or blood vessel distribution and transplant outcome was analyzed. The combined blockade promotes 90% survival of high-risk transplants. The host beds were specifically modified by selective inhibition of lymphangiogenesis but not hemangiogenesis. A strong correlation was also identified between high-risk transplant rejection and severe lymphatic invasion reaching the donor-graft border.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reducing the occurrence of lymphangiogenesis in a corneal transplant subject having inflamed and vascularized high risk of rejection, the method comprising:
   administering to the subject an amount of:
      a first antagonist for VEGFR-3, wherein the first antagonist is a neutralizing antibody or binding fragment thereof that specifically binds to VEGFR-3; and
      a second antagonist for VLA-1, wherein the second antagonist is a neutralizing antibody or binding fragment thereof that specifically binds to VLA-1;
   effective to reduce the occurrence of lymphangionesesis in a corneal transplant in the subject having a high risk of rejection.

2. The method according to claim 1, wherein the first and second antagonists are neutralizing antibodies.

3. The method according to claim 1, wherein the corneal transplant subject has an inflamed and vascularized cornea.

4. The method according to claim 1, further comprising transplanting corneal tissue in the subject.

5. The method according to claim 1, further comprising transplanting tissue in a graft bed of the subject.

6. The method according to claim 5, wherein the administering is performed prior to the transplanting.

7. The method according to claim 5, wherein the administering is performed during the transplanting.

8. The method according to claim 5, wherein the administering is performed after the transplanting.

9. The method according to claim 5, wherein the graft bed of the subject is inflamed and vascularized.

10. The method according to claim 9, wherein the method comprises reducing inflammatory lymphangiogenesis in the graft bed.

11. The method according to claim 1, wherein the first and second antagonists are administered simultaneously.

12. The method according to claim 1, wherein the first and second antagonists are administered sequentially.

13. The method according to claim 5, wherein the method comprises reducing inflammatory lymphangiogenesis at a grafting border between the transplanted tissue and the graft bed.

14. The method according to claim 5, wherein the method comprises reducing the occurrence of opacity of the corneal tissue.

15. The method according to claim 5, wherein the method does not significantly inhibit blood vessel growth in the tissue.

16. The method according to claim 15, wherein the method comprises inhibiting lymphatic vessel growth into the transplanted tissue.

17. The method according to claim 4, wherein the method comprises enhancing survival of the transplanted organ in the subject.

18. The method according to claim 5, wherein the method comprises enhancing survival of the transplanted tissue in the subject.

19. The method according to claim 18, wherein the method comprises reducing inflammatory lymphangiogenesis of the corneal tissue.

20. The method according to claim 18, wherein the method comprises reducing the occurrence of opacity of the corneal tissue.

21. The method according to claim 19, wherein the method does not significantly inhibit blood vessel function in the tissue.

22. The method according to claim 18, wherein the method comprises inhibiting lymphatic vessel function in the tissue.

* * * * *